(12) United States Patent
Krog

(10) Patent No.: US 6,901,956 B2
(45) Date of Patent: Jun. 7, 2005

(54) FLOW CELL HAVING ENDLESS LOOP MANIFOLD

(75) Inventor: Jens Krog, Ulstrup (DK)

(73) Assignee: Danfoss A/S (DK)

( * ) Notice: Subject to any disclaimer, the term of this patent is extended or adjusted under 35 U.S.C. 154(b) by 289 days.

(21) Appl. No.: 10/386,336

(22) Filed: Mar. 10, 2003

(65) Prior Publication Data

US 2003/0168107 A1 Sep. 11, 2003

Related U.S. Application Data

(63) Continuation-in-part of application No. 10/014,280, filed on Dec. 11, 2001, now Pat. No. 6,557,582, which is a continuation of application No. PCT/DK00/00317, filed on Jun. 14, 2000.

(30) Foreign Application Priority Data

Jun. 18, 1999 (DE) .......................................... 199 27 850

(51) Int. Cl.[7] ............................................... F16K 11/24
(52) U.S. Cl. .................... 137/599.03; 137/896
(58) Field of Search .......................... 137/599.03, 602, 137/603, 606, 599.04, 896, 897, 898, 561 A

(56) References Cited

U.S. PATENT DOCUMENTS

| | | | | |
|---|---|---|---|---|
| 391,647 A | * | 10/1888 | Reid ...................... 137/599.03 |
| 2,828,766 A | | 4/1958 | Postmus | |
| 3,306,587 A | * | 2/1967 | Schroedter .................. 137/602 |
| 3,347,534 A | * | 10/1967 | Dawson ...................... 137/897 |
| 3,690,833 A | | 9/1972 | Ferrari | |
| 4,207,919 A | * | 6/1980 | Hutton .................. 137/599.04 |
| 4,816,083 A | * | 3/1989 | Bangyan ................ 137/599.03 |
| 4,915,123 A | * | 4/1990 | Morgovsky et al. ... 137/599.04 |
| 5,431,185 A | | 7/1995 | Shannon et al. | |
| 5,590,686 A | * | 1/1997 | Prendergast ................ 137/597 |
| 5,599,503 A | | 2/1997 | Manz et al. | |
| 5,695,719 A | | 12/1997 | Lynggaard et al. | |
| 6,557,582 B2 | * | 5/2003 | Krog ..................... 137/599.03 |

FOREIGN PATENT DOCUMENTS

| | | |
|---|---|---|
| CH | 646 503 | 11/1984 |
| DE | 24 36 113 | 2/1976 |
| DE | 196 48 685 | 6/1997 |
| EP | 0 047 130 | 10/1982 |
| EP | 0 412 046 | 6/1991 |

OTHER PUBLICATIONS

Berg et al., *"Miniaturized Chemical Analysis Systems"*, Proceedings, 1994 5th International Symposium, Oct. 2–4, 1994, pp. 181–184, XP002901273, figs. 1, 6, 7.

* cited by examiner

Primary Examiner—Stephen M. Hepperle
(74) Attorney, Agent, or Firm—Altera Law Group, LLC

(57) ABSTRACT

Disclosed herein is a flow cell having an endless loop manifold. The flow cell includes at least two inlet channels. The inlet channels are each connectable with a reservoir and controllable by means of valves. The inlet channels end in an inlet chamber. Each of two ends of the inlet chamber is connected with a discharge channel by means of outlet channels. Old fluid remaining in the inlet chamber is displaced into the discharge channel by newly supplied fluid. Dead time waiting until the old fluid has been displaced by the pure new fluid is minimal.

7 Claims, 2 Drawing Sheets

FLOW CELL HAVING ENDLESS LOOP MANIFOLD

CROSS REFERENCE TO RELATED APPLICATION

This application is a Continuation-in-Part of the following and commonly assigned U.S. Patent Application, which is hereby incorporated herein by reference in its respective entirety:

"FLOW CELL" to Krog, having U.S. patent application Ser. No. 10/014,280 filed Dec. 11, 2001 now U.S. Pat. No. 6,557,582, which is a continuation of international application serial number PCT/DK00/00317 filed on 14 Jun. 2000 and published as WO 00/79286 A1 on 28 Dec. 2000.

BACKGROUND OF THE INVENTION

1. Field of the Invention

The invention relates in general to a flow cell with at least two inlet channels. Each of the inlet channels is connectable with a reservoir and controllable by means of valves. The inlet channels end in an inlet chamber. The inlet chamber has a common discharge channel.

2. Description of Related Art

Flow cells are known to be used in micro systems for chemical analysis techniques. This concerns planar micro systems having substrates of glass, silicium, plastic or other materials. These systems are also known under the name "Lab on a chip". They have built-in micro-valves, channels for fluid transport, and reservoirs for fluid. The channel structure can be produced by etching, milling, boring, die-casting, hot embossing, and other methods.

It is a disadvantage of prior systems that the latest transported fluid always remains in the chamber where it pollutes the next fluid to be transported. Rather long dead times are required before an analysis can be made with a new fluid. The first mentioned fluid remains in corners and dead spaces making complete removal extremely difficult. This is especially common when more than two inlet channels are utilized.

In an infusion arrangement as shown in U.S. Pat. No. 5,431,185, it is disclosed that drugs are added to the infusion solution via three inlet channels, the channels being controllable by valves. Pollution is avoided because the continuously incoming infusion solution acts as rinsing fluid.

Previous flow cells included multiple inlet channels, one or several discharge channels, and a cell structure constituted by a single line channel. In a flow cell structure having a single line channel, a shift of fluid ingress into the flow cell from a first inlet channel to inlet channels more advanced in the flow cell would result in a dead space volume in the channel portion extending between more advanced inlet channels and the initial inlet channel. Significant disadvantages result from this dead space volume, such as, increased rinsing time and impurities in the fluid leaving the flow cell at discharge channel. The previous flow cells suffered these disadvantages and dead end spaces resulted in the flow cell which were difficult to rinse out causing long rinsing times and creating the risk of impure fluid volumes.

It can be seen that there is a need for a flow cell having an endless loop manifold to avoid and eliminate dead end spaces, reduce rinsing times, and improve fluid purity.

SUMMARY OF THE INVENTION

The instant invention discloses providing a flow cell in which the pollution risk is drastically reduced and dead time until a new fluid is available in a pure condition is substantially reduced.

According to the invention, the pollution risk and dead time is overcome by a flow cell having an endless loop manifold wherein each of the two ends of the inlet chamber is connected with a discharge channel via an outlet channel.

New incoming fluid flows to both outlet channels and therefore pushes out all of the old fluid through the ends of the inlet chamber and the outlet channels to the discharge channel. The new fluid, regardless from which inlet channel it flows into the inlet chamber, is therefore a rinsing medium for the old fluid resulting in decreasing the dead time until the passing of pure new fluid. The inlet chamber and outlet channels are dimensioned to avoid the creation and occurrence of dead spaces.

It is advantageous that the inlet chamber has a width, which is small in comparison with the length measured between the inlet chamber ends. The new fluid flows past and against ends of the other inlet channels in the inlet chamber, which provides a good cleaning effect to evacuate the contents of the chamber. It is preferable that the width of the inlet chamber be less than $\frac{1}{5}$ the length of the inlet chamber, and more preferably less than $\frac{1}{10}$ of the length.

It is also preferable that the last section of each inlet channel be formed by an inlet channel valve. The new fluid therefore passes immediately through the closing member, which improves the rinsing effect.

Another advantage occurs with a suitable choice of flow resistances of inlet chamber and outlet channels. It is preferable that the flow resistance of each outlet channel is at least $\frac{1}{5}$ of the flow resistance of the inlet chamber between the ends of the inlet chamber. The flow resistance can be expressed by the equation bar/(l/s), where bar indicates the pressure, I indicates the flow quantity and s indicates the time. The desired flow resistances can easily be obtained through a suitable selection of the cross section and the length of the outlet channels.

It is also advantageous to provide the inlet chamber with inlet channels on an inlet side, the discharge channel on the outlet side, and between the inlet and outlet sides to provide an island-like restriction element, which restricts flow from the inlet chamber to the two outlet channels. The inlet chamber and inlet and outlet channels can be planarly dimensioned. Two dimensional embodiments substantially simplify production over three-dimensional embodiments and are particularly relevant for use in micro systems.

The inlet chamber and the restriction element are configured to have a generally rectangular shape to simplify production and provide greater dimensional accuracy.

The inlet chamber with inlet channel ends and the outlet channels are arranged symmetrically to the connection of the discharge channel. This symmetry provides substantially the same conditions on cleaning the chamber with a subsequent fluid.

It is preferable that at least three inlet channels end in the inlet chamber. Therefore, more than two fluids can be introduced into the inlet chamber at the same time.

It is expedient that the first section of the discharge channel be formed by a micro pump so that the micro flow cell can be kept small.

It is preferable that four micro valves are connected with the inlet chamber. The length of the inlet chamber is associated with the length of the outlet channels and/or the arrangement of the micro pump and subsequently, the two outlet channels.

A preferred use of the micro flow cell of the instant invention is in a chemical micro analysis system because several opportunities for performing different measurements at relatively short intervals are presented. For example, the micro flow cell is adapted for water analyses in a sewage plant.

The foregoing objects, advantages and distinctions of the invention, among other, are obtained in a presently preferred construction that provides a flow cell having an endless loop manifold.

These and various other advantages and features of novelty which characterize the invention are pointed out with particularity in the claims annexed hereto and form a part hereof. However, for a better understanding of the invention, its advantages, and the objects obtained by its use, reference should be made to the drawings which form a further part hereof, and to accompanying descriptive matter, in which there are illustrated and described specific examples of an apparatus in accordance with the invention.

BRIEF DESCRIPTION OF THE DRAWINGS

Referring now to the drawings in which like reference numbers represent corresponding parts throughout.

DETAILED DESCRIPTION OF THE INVENTION

In the following description of the exemplary embodiment, reference is made to the accompanying drawings which form a part hereof, and in which is shown by way of illustration the specific embodiment in which the invention may be practiced. It is to be understood that other embodiments may be utilized as structural changes may be made without departing from the scope of the present invention.

The present invention provides a flow cell having an endless loop manifold. The flow cell has at least two inlet channels. Each of the inlet channels is connectable with a reservoir and controllable by means of valves. The inlet channels end in an inlet chamber. The inlet chamber has two outlet channels that end at a common discharge channel.

Figure 1:
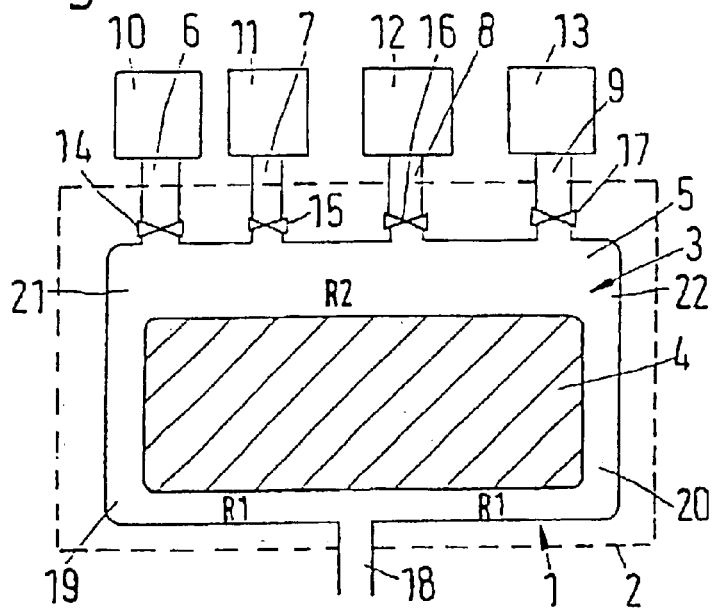
FIG. 1 illustrates a schematic view of the micro flow cell according to an embodiment of the invention.

FIG. 1 illustrates a schematic view of the micro flow cell according to an embodiment of the invention. In FIG. 1, a micro flow cell 1 is formed on a chip. The chip consists of a substrate of silicon or the like, having on its surface indentations, which are covered by an additional layer, which also contains active elements. An approximately rectangular chamber 3 is provided, in which residual material forms an equally, approximately rectangular, island-like restriction element 4. On one side of chamber 3, four inlet channels 6, 7, 8 and 9, each connected with a reservoir 10, 11, 12 and 13 for fluids, end in an inlet chamber 5 of chamber 3.

Disposed in the last section of each inlet channel is a controllable micro valve 14, 15, 16 and 17. A discharge channel 18 is arranged in another side of the chamber 3 lying on the opposite side of the restriction element 4 and opposite the inlet chamber 5. The chamber 3, the inlet channels 6–9 and the discharge channel 18 lie substantially in one plane, forming a generally two dimensional system.

The restriction element 4 is arranged in the chamber 3 in such a way that at adjacent opposing ends 21, 22 of the inlet chamber 5 there are disposed two outlet channels 19 and 20, which extend from the ends 21, 22 of the inlet chamber 5 around the restriction element 4 and ending at the discharge channel 18 forming a manifold structure 2 outlined by dashed line.

The manifold structure 2 is in the form of a closed endless loop, where the fluid flow coming from any of the inlet channels 6–9 enters the inlet chamber 5 and is divided into two flow paths around the restriction element 4 into the two outlet channels 19, 20 and recombined on the other side of the restriction element 4 in the discharge channel 18. Although a single discharge channel 18 is disclosed multiple discharge channels may be utilized.

As can be clearly discerned in FIG. 1, no dead end spaces exist in the endless loop manifold 2 facilitating fast rinsing and exchanging of old fluid with new fluid. The entire fluid content of the inlet chamber 5 is exchanged substantially unchanged through the outlet channels 19, 20. The endless loop manifold 2 facilitates removal of old fluid from the flow cell 1 by displacing an entire volume of old fluid with a volume of new fluid. The old fluid flows through the outlet channels 19, 20 and the discharge channel 18 out of the flow cell 1 leaving new fluid in the flow cell.

Each of the two outlet channels 19 and 20 has a flow resistance R1, which is larger than the flow resistance R2 of inlet chamber 5. Preferably, the flow resistance is multiple times larger. Desirable flow effects also occur when a smaller flow resistance exists in the outlet channels 19 and 20 than in the inlet chamber 5.

Figure 2:
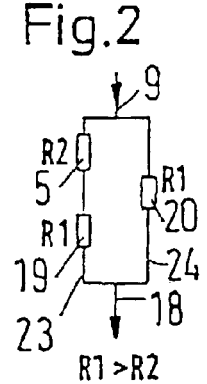
FIG. 2 illustrates a fluid flow circuit diagram through the flow cell according to an embodiment of the invention.

FIG. 2 illustrates a fluid flow circuit diagram through the flow cell having an endless loop manifold according to an embodiment of the invention. In FIG. 2, when opening one of the micro valves, for example the micro valve 17, the flow through the manifold is given in the circuit diagram as shown in FIG. 2. There are two parallel branches 23 and 24 between the end of the inlet channel 9 and the discharge channel 18. The first branch 23 has a flow resistance R1+R2, which is only slightly larger than the flow resistance R1 of the branch 24.

The fluid from the inlet channel 9 passes through micro valve 17, flows into inlet chamber 5, and passes off through both branches 23, 24, thereby displacing any remaining volume of a previously supplied different fluid remaining in chamber 3. After a short while, the fluid supplied via the inlet channel 9 from micro valve 17 flows off in pure form through the discharge channel 18. The same result occurs upon opening another micro valve, such as, 14, 15 or 16.

Figure 3:
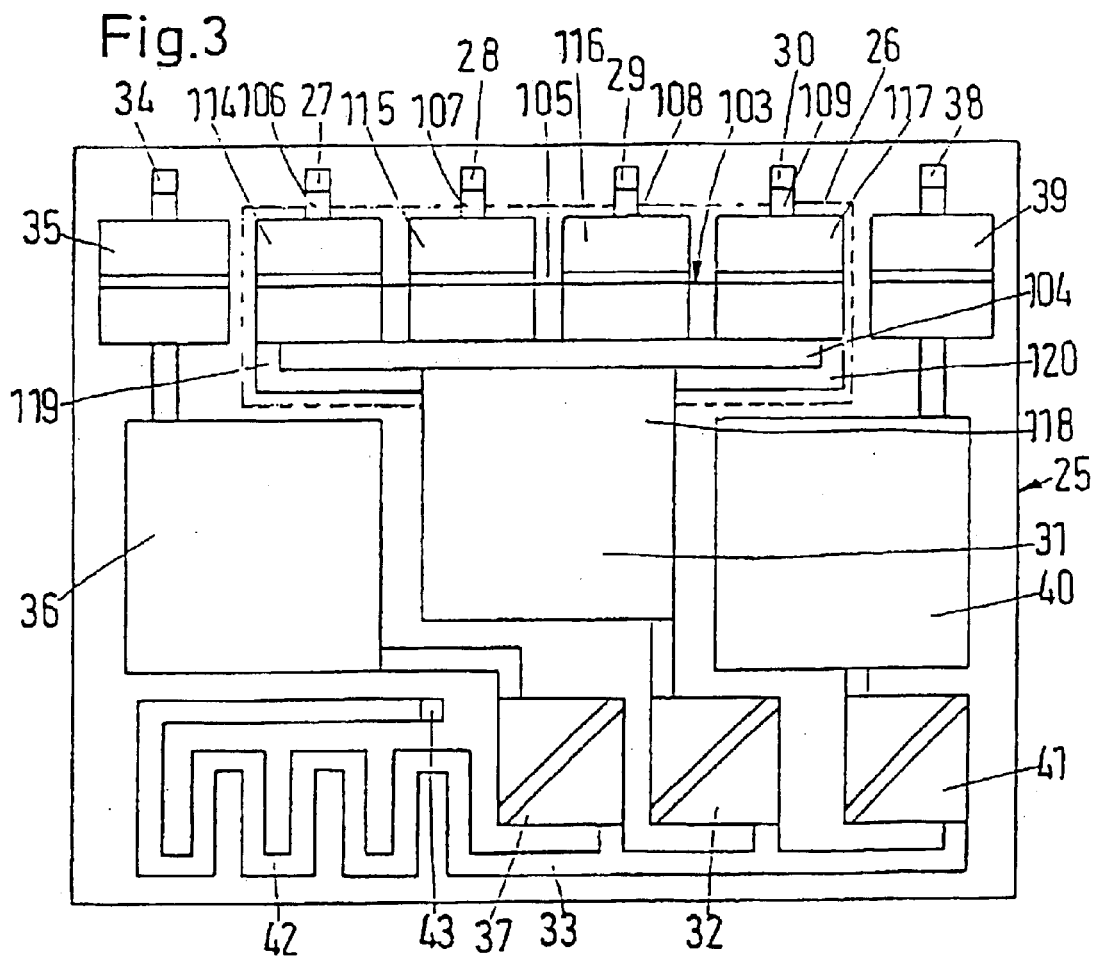
FIG. 3 illustrates a micro chip employing the micro flow cell according to an embodiment of the invention.

FIG. 3 illustrates a micro chip employing the micro flow cell according to an embodiment of the invention. FIG. 3 shows a micro chip 25 with the approximate dimensions 8×10 $mm^2$ having a chemical micro analysis system for water analysis in a sewage plant. The area 26 surrounded by dotted lines substantially corresponds to the micro flow cell 1 illustrated in FIG. 1.

Corresponding parts, i.e., reference numbers, have been increased by 100 and are used to identify similar components. Disclosed in FIG. 3 is a chamber 103 having an island-like restriction element 104 making it possible to easily distinguish between inlet chamber 105 and two outlet channels 119 and 120. Inlet channels 106, 107, 108 and 109 are provided with plug connections 27, 28, 29 and 30, which serve to connect the inlet channels with reservoirs 10,11,12 and 13, as shown in FIG. 1.

Disposed in the last section of the inlet channels 106-109 are micro valves 114, 115, 116 and 117, whose outlet part extends partially into inlet chamber 105. A first section of discharge channel 118 is formed by a micro pump 31, which extends partially into and overlaps the outlet channels 119, 120. The micro flow cell 1 is adapted and configured to act as an inlet valve for the micro pump 31.

The discharge channel 118 leads through the micro pump 31 and an additional micro valve 32 to an outlet channel 33. Outlet channel 33 may also receive an additional fluid from connection 34 through another micro valve 35, another micro pump 36, and a micro valve 37, as well as from another connection 38 through micro valve 39, micro pump 40 and micro valve 41. Fluid mixing subsequently takes place in a meandering square wave shaped channel 42 which leads to connection 43. A light cell arrangement can be connected to connection 43 wherein photo spectroscopy can be performed on the fluid.

The inlet channel 8 may carry a test fluid, the inlet channels 6, 7 and 9 may each carry a reagent. Through connections 38 and 34, the fluids to be examined may be added. The capacity of such a microanalysis system amounts to approximately 0.1 to 100 micro litres per minute.

Micro valves and micro pumps may be operated piezoelectrically. However, other ways of energizing the system are possible, for example with compressed air.

Figure 4:
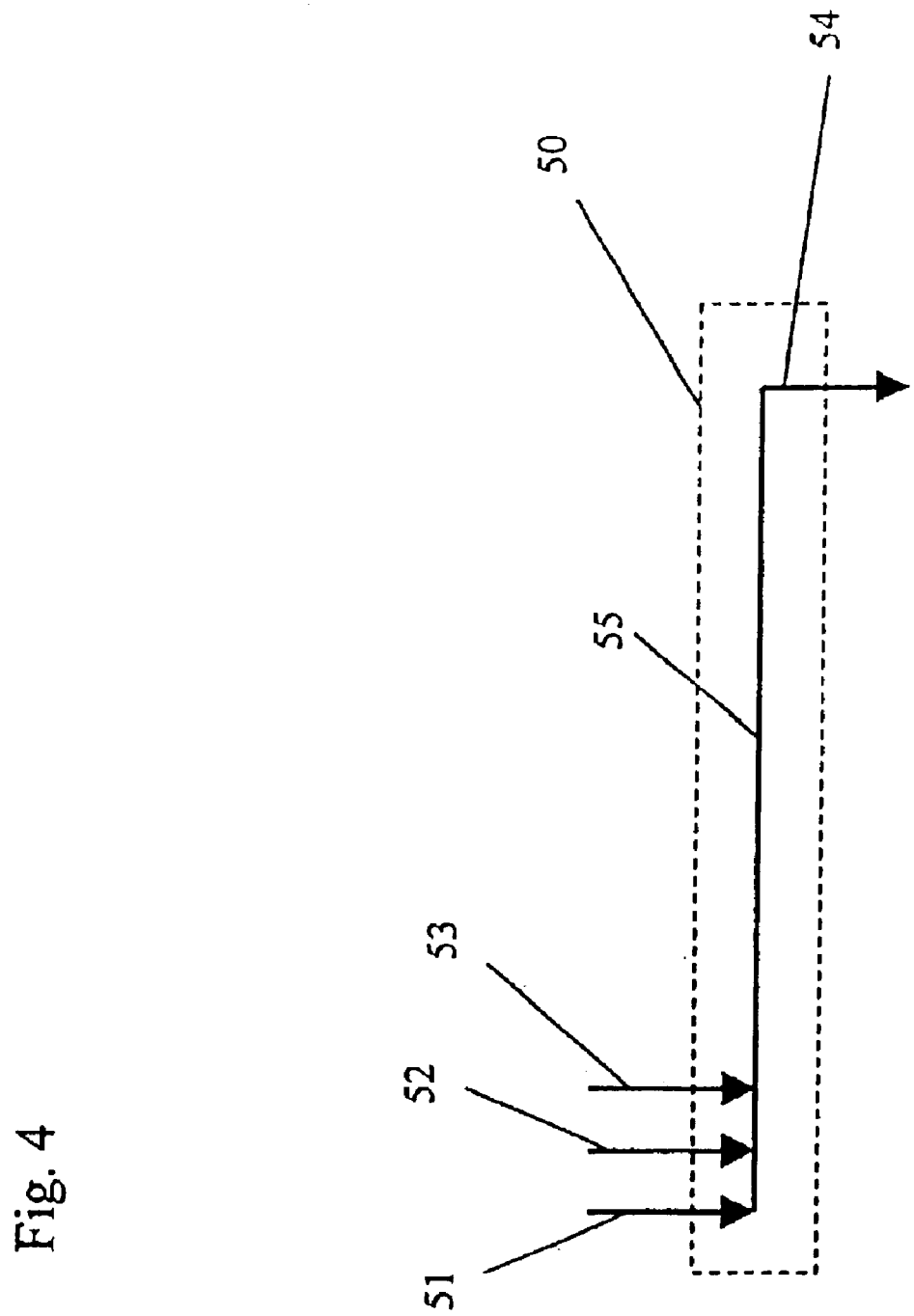
FIG. 4 illustrates a flow cell structure having a single line channel.

FIG. 4 illustrates a disadvantageous flow cell structure having a single line channel 55. In FIG. 4, a shift of fluid ingress into the flow cell 50 from inlet channel 51 to inlet channels 52 or 53 would result in a dead space volume in the channel portion extending between inlet channels 51 or 52, and inlet channel 53. Significant disadvantages result from this dead space volume, such as, increased rinsing time and impurities in the fluid leaving the flow cell at discharge channel 54.

The use of the micro flow cell is not limited to chemical analysis systems. It can be used anywhere, where one or several different fluids must be added, and where a fluid change must be rapid and cause short dead times until the supply of the newly added fluid in pure form is established.

The flow cell according to the invention can also be realized in different ways, for example, where the inlet chamber and the outlet channels are made of hoses.

The foregoing description of the exemplary embodiment of the invention has been presented for the purposes of illustration and description. It is not intended to be exhaustive or to limit the invention to the precise form disclosed. Many modifications and variations are possible in light of the above teaching. It is intended that the scope of the invention be limited not with this detailed description, but rather by the claims appended hereto.

What is claimed is:

1. A flow cell comprising:

an endless loop manifold, the endless loop manifold including a plurality of inlet channels, each of the inlet channels connectable with a reservoir and controllable by a valve, the inlet channels end in an inlet chamber, the inlet chamber having an outlet channel at each of opposing ends of the inlet chamber, the outlet channels dividing a fluid flow around a closed loop and recombining the fluid flow at an at least one common discharge channel.

2. The flow cell according to claim 1, wherein the closed loop is formed by a restriction element disposed between the inlet channels and the discharge channel.

3. The flow cell according to claim 2, wherein the restriction element delineates the closed loop and is bounded on opposing sides by the outlet channels.

4. The flow cell according to claim 1, wherein the inlet channels and at least a portion of the outlet channels are arranged generally parallel to the discharge channel.

5. The flow cell according to claim 1, wherein the inlet chamber has a length which is arranged generally perpendicular to the inlet channels and the discharge channel.

6. The flow cell according to claim 1, wherein the endless loop manifold further comprises a restriction element bounded on one side by the inlet chamber, the restriction element being surrounded by the outlet channels on at least three sides, and the endless loop manifold discharging fluid into the discharge channel on a side opposite the inlet chamber.

7. The flow cell according to claim 1, wherein the endless loop manifold facilitates removal of old fluid from the flow cell by displacing an entire volume of old fluid with a volume of new fluid, the old fluid flows through the outlet channels and the discharge channel out of the flow cell leaving new fluid in the flow cell.

* * * * *